United States Patent [19]

Reiter et al.

[11] Patent Number: 5,769,834
[45] Date of Patent: Jun. 23, 1998

[54] ABSORBENT ARTICLE HAVING A FLUID PUMPING ELEMENT

[75] Inventors: Godfrey Reiter, Cincinnati; John Billings Burchnall, West Chester, both of Ohio

[73] Assignee: The Procter & Gamble Company, Cincinnati, Ohio

[21] Appl. No.: 746,934

[22] Filed: Nov. 18, 1996

[51] Int. Cl.[6] .................................................. A61F 13/15
[52] U.S. Cl. ...................................... 604/385.1; 604/378
[58] Field of Search .................................... 604/358, 378, 604/383, 385.1, 354, 331; 128/761, 762

[56] References Cited

U.S. PATENT DOCUMENTS

| | | |
|---|---|---|
| 810,119 | 1/1906 | Green . |
| 3,491,759 | 1/1970 | Samuel .................................... 604/378 |
| 3,889,679 | 6/1975 | Taylor . |
| 3,929,135 | 12/1975 | Thompson . |
| 4,246,901 | 1/1981 | Michaud ................................ 128/761 |
| 4,676,785 | 6/1987 | Battista . |
| 4,778,459 | 10/1988 | Fuisz . |
| 4,795,453 | 1/1989 | Wolfe . |
| 4,865,597 | 9/1989 | Mason, Jr. et al. . |
| 4,886,513 | 12/1989 | Mason, Jr. et al. . |
| 5,062,839 | 11/1991 | Anderson . |
| 5,078,710 | 1/1992 | Suda et al. . |
| 5,151,091 | 9/1992 | Glaug et al. . |
| 5,169,394 | 12/1992 | Jean . |
| 5,268,213 | 12/1993 | Murakami et al. . |
| 5,290,262 | 3/1994 | Vukos et al. . |
| 5,300,053 | 4/1994 | Genaro . |
| 5,324,278 | 6/1994 | Visscher et al. . |
| 5,342,337 | 8/1994 | Runeman et al. . |
| 5,366,451 | 11/1994 | Levesque ................................. 604/378 |
| 5,391,160 | 2/1995 | Runeman et al. . |

FOREIGN PATENT DOCUMENTS

4129553  4/1992  Japan .

Primary Examiner—Robert A. Clarke
Attorney, Agent, or Firm—William Scott Andes; E. Kelly Linman; Jacobus C. Rasser

[57] ABSTRACT

An absorbent article useful for absorbing bodily fluids discharged by the wearer of the article is provided. The absorbent article comprises a fluid pervious topsheet, a fluid impervious backsheet affixed to the topsheet, an absorbent core disposed between the topsheet and the backsheet, and a resilient tubular member disposed between the topsheet and the backsheet for transporting the fluids to a predetermined region of the core. The tubular member has a plurality of fluid inlets and a plurality of fluid outlets, the inlets and outlets providing fluid communication between the interior and exterior of the tubular member. Discharged fluids may be transported from regions adjacent the inlets into the interior of the tubular member, and thereafter through the outlets to the predetermined regions of the core adjacent the outlets, thereby rapidly transporting the fluids to the predetermined region of the core. The inlets are normally open and the outlets are normally closed, however compression of the tubular member causes the inlets to close and the outlets to open, thereby permitting the desired fluid movement. Decompression and compression of the tubular member may be accomplished by the normal bodily movements of the wearer.

25 Claims, 3 Drawing Sheets

ABSORBENT ARTICLE HAVING A FLUID PUMPING ELEMENT

BACKGROUND OF THE INVENTION

1. Field of the Invention

The present invention relates generally to an absorbent article for the acquisition and storage of discharged bodily fluids, and more specifically to an absorbent article having a passive fluid pumping element contained therein.

2. Description of Related Art

Absorbent articles for the acquisition and storage of discharged bodily fluids (urine, vaginal discharge, etc.) are well known in the prior art, and have been provided in various configurations. These devices include, for example, diapers, incontinence pads, sanitary napkins, and pantyliners. Nearly all such devices in current use comprise a fluid pervious topsheet, a fluid impervious backsheet affixed to the topsheet, and an absorbent core disposed between the topsheet and the backsheet. The topsheet is placed against, or in close proximity to the body of the wearer in the location of fluid discharge, and permits discharged fluids to transfer through its thickness into the absorbent core. The backsheet prevents fluids from escaping from the absorbent article.

The absorbent core is designed to both absorb and store discharged bodily fluids which pass through the topsheet. Absorbent cellulosic fibers are often employed in the core, however, recently various superabsorbent polymeric materials have become popular. These superabsorbent materials include polymers which absorb bodily fluids to form a hydrogel (absorbent gelling material), and these superabsorbents are typically disbursed throughout the core in conjunction with more traditional cellulosic materials. Alternatively, the absorbent core can comprise multiple layers or regions or varying absorption and storage properties.

Of course, the absorbent cores of the prior art do not have an unlimited capacity, and this capacity is often limited by their inability to distribute absorbed fluids over the largest volume of the core possible. Bodily fluids, however, are usually discharged from discreet locations, and the absorbent core adjacent to the discharge area may become overloaded. Ideally, the absorbent core will quickly redistribute the fluid away from the discharge area in order to avoid overload, and insure the comfort of the wearer. Adequate distribution of the fluids over as wide an area as possible is particularly critical when absorbent gelling materials are employed, as gel blocking may occur. Gel blocking occurs when the absorbent gelling material swells with fluids, at least partly blocking fluid passageways, hence inhibiting liquids from being distributed to other absorbent materials further away in the core. Once gel block occurs, transmission of fluids through the absorbent gelling material becomes very slow, and the absorbent article may fail to perform satisfactorily long before the absorbent core has reached its fluid capacity. In addition, absorbent articles of the prior art typically are narrowest in the portion intended to be worn adjacent the crotch region. Since fluids are usually discharged in this region and tend to spread across the absorbent article from the point of discharge, the edge portions of the absorbent articles in the crotch region may become overloaded, thereby leading to side soiling.

Thus, there is a need for absorbent articles useful for absorbing discharged bodily fluids having a means for insuring rapid and equal distribution of the fluids throughout the absorbent core, as well as a means for preventing side soiling.

SUMMARY OF THE INVENTION

It is an object of the present invention to provide an improved absorbent article for the acquisition and storage of discharged bodily fluids.

It is another object of the present invention to provide an absorbent article for the acquisition and storage of discharged bodily fluids, wherein a means for rapidly transporting fluids to a predetermined region of the absorbent core is provided.

It is yet another object of the present invention to provide an absorbent article for the acquisition and storage of discharged bodily fluids, wherein the means for rapidly transporting fluids also provides side soiling protection.

The foregoing objects can be accomplished, in accordance with one embodiment of the present invention by providing an absorbent article for absorbing discharged bodily fluids comprising:

(a) a fluid pervious topsheet;

(b) a fluid impervious backsheet affixed to the topsheet;

(c) an absorbent core disposed between the topsheet and the backsheet; and (d) a tubular member disposed between the topsheet and the backsheet for delivering the fluids to a predetermined region of said core.

The tubular member preferably has a plurality of fluid inlets and a plurality of fluid outlets, and these inlets and outlets provide fluid communication between the interior and exterior of the tubular member. The tubular member is configured and positioned so as to permit bodily fluids to pass through the inlets into the interior of the tubular member, and thereafter out of the interior and through the outlets into the predetermined regions of said core. In this manner, bodily fluids can be quickly transported from a point adjacent the fluid inlets to a predetermined region of the core adjacent the fluid outlets without reliance upon the wicking or diffusion properties of the core material.

The fluid inlets of the tubular member are substantially open and the outlets may be open or substantially closed when no distortive or compressive force is applied to the tubular member, thereby permitting the fluids to enter the interior of the tubular member through the inlets. Preferably, however, the outlets remain substantially closed when no distortive or compressive force is applied. The fluid outlets are selectively opened (or remain open) in response to a distortive force applied to the tubular member, thereby permitting fluids to exit from the interior of the tubular member through the fluid outlets. The inlets are preferably selectively closed in response to a distortive force, such that repeated application and removal of a distortive force to the tubular member results in the transportation of the fluids through the inlets into the interior of the tubular member, and thereafter out of the interior through the outlets. Since the article is preferably configured to be positioned in the crotch region, the tubular member may be positioned such that this distortive or compressive force may be supplied by normal bodily movements.

The fluid inlets and outlets may have any of a number of configurations. For example, the inlets may comprise slits having a length which is substantially parallel to the longitudinal axis of the tubular member and extends along at least the top (or body facing side of the article), or more preferably at least one side of the tubular member. The outlets preferably extend across the bottom portion of the tubular member, and may also comprise slits having a length which is substantially parallel to the longitudinal axis of the tubular member such that a compressive force applied to the top portion of the tubular member will cause the inlets to substantially close and the outlets to substantially open (or remain open). Alternatively, the outlets may comprise a series of regularly or irregularly shaped holes.

The tubular member is also preferably segmented such that it has a plurality of compartments in order to facilitate proper fluid flow. The tubular member also may be positioned at least partially within the absorbent core, or entirely within the absorbent core. In order to facilitate proper fluid flow, the inlets and/or outlets may also have at least one check-valve flap. Check-valve flaps on the inlets are configured so as to prevent fluids from escaping the interior of the tubular member through the inlets when the tubular member is compressed, and check-valve flaps on the outlets are configured to prevent expelled fluids from reentering the tubular member through the outlets. Finally, the tubular member may comprise a length of resilient polymeric tubing. Alternatively, the tubular member may comprise a thin polymeric film surrounding a porous internal filler material, such that the filler material comprises the interior of the tubular member and the inlets and outlets are formed in the film.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DESCRIPTION OF THE PREFERRED EMBODIMENTS

The present invention is directed towards absorbent articles which are intended to absorb and retain fluids, such as those discharged from the body (e.g., urine, blood, vaginal discharges and the like), and in particular, feminine hygiene pads (e.g., sanitary napkins and pantyliners), diapers and incontinence pads. These particular absorbent articles are designed to be placed against or in close proximity to the crotch region of the wearer, and absorb fluids discharged in this region.

Figure 1:
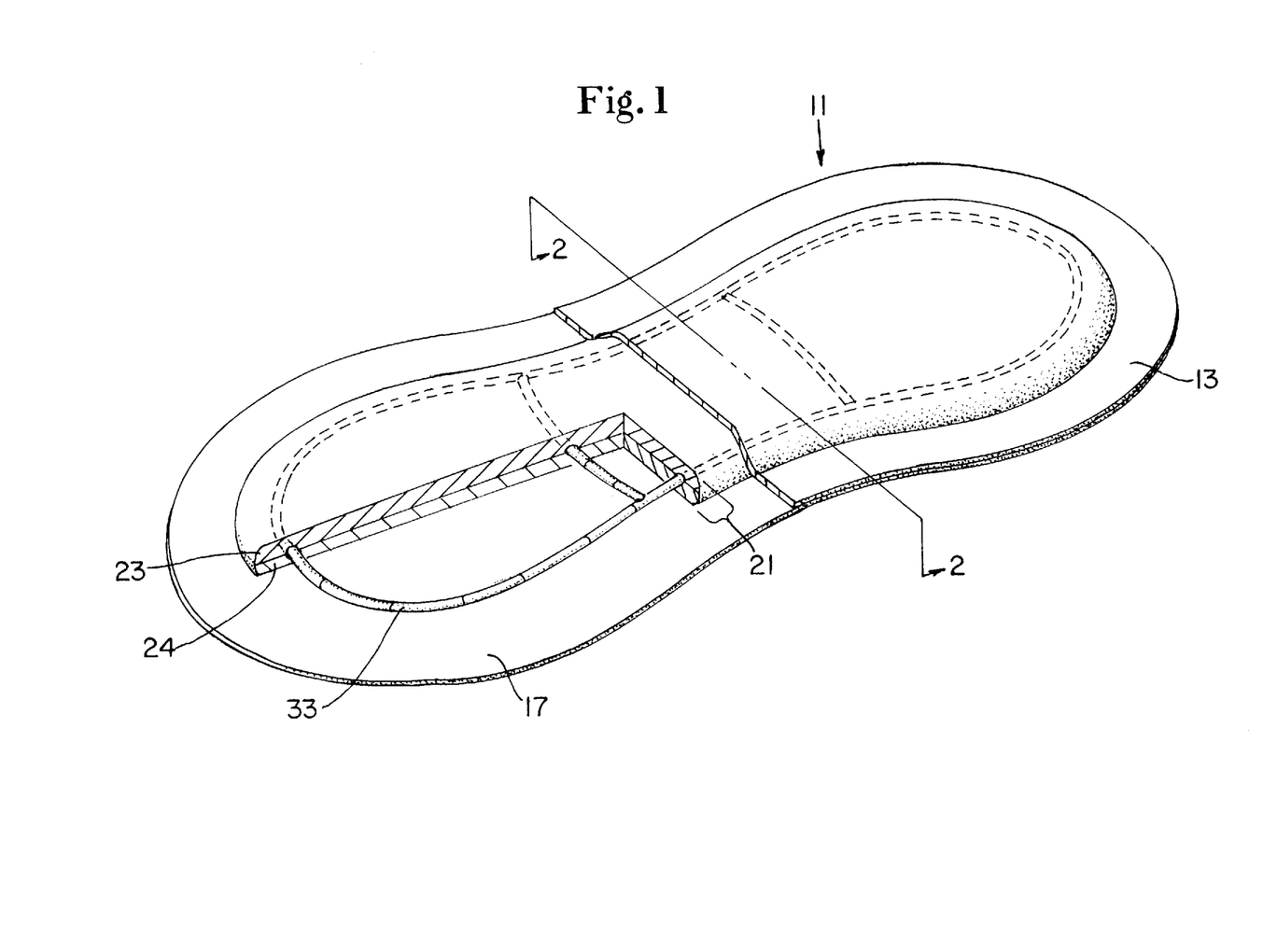
FIG. 1 a partially cut-away view of a sanitary napkin made in accordance with the present invention.
Figure 2:
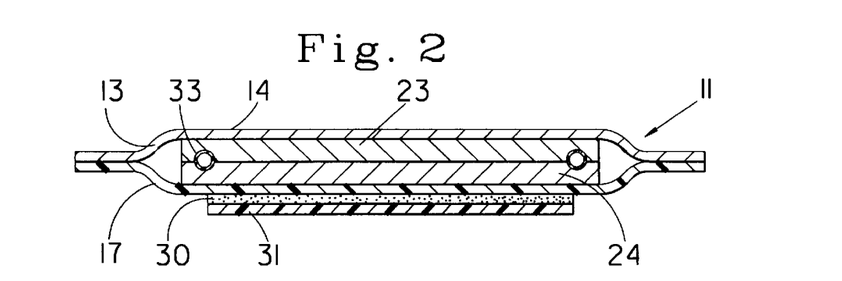
FIG. 2 is a cross-sectional view of the sanitary napkin of FIG. 1, taken along line 2—2 thereof.

Referring now to the drawings, wherein like numerals indicate similar elements throughout the views, one particular absorbent article of the present invention is shown in FIG.'s 1 and 2 as a sanitary napkin 11. Like most absorbent articles utilized for absorbing and retaining discharged bodily fluids, sanitary napkin 11 has a liquid pervious topsheet 13, a liquid impervious backsheet 17, and an absorbent core 21 disposed between topsheet 13 and backsheet 17. In the embodiment of FIG. 1, topsheet 13 and backsheet 17 are shown as being coextensive in area, and have a generally peanut-shaped configuration. As is well known in the art, various other shapes may be employed for the sanitary napkin shown in FIG. 1, including a rectangular shape, a dog-bone shape, an hourglass shape, a sinusoidal shape, or an elongated pear shape. The shape of sanitary napkin 11 is chosen so as to cover the greatest possible area in the crotch portion of a wearer's undergarment, while still being comfortable.

Topsheet 13 and backsheet 17 also preferably have a shape which is somewhat larger than that of absorbent core 21 so that the edge portions of topsheet 13 and backsheet 17 which extend beyond absorbent core 21 may be affixed to each other in any manner known in the art. Thus, topsheet 13 and backsheet 17 may be affixed to each other by means of glue, crimping or heat sealing about the entire periphery of each. In this manner, absorbent core 21 is sealed between topsheet 13 and backsheet 17. Sanitary napkin 11 is also shown as having an adhesive strip 30 secured to the exterior surface (or garment-facing side) of backsheet 17 for securing sanitary napkin 11 to the undergarment of the wearer. A peel-off cover 31 is releasably affixed to adhesive strip 30, such that cover 31 may be removed by the user in order to expose adhesive strip 30. Various other configurations for adhesive strip 30 and cover 31 may be employed, as is known to those skilled in the art.

Although the above description generally pertains to sanitary napkin 11 of FIGS. 1 and 2, this same general structure of an absorbent core disposed between a fluid pervious topsheet and a fluid impervious backsheet can also be employed in other absorbent articles such as pantyliners, diapers and incontinence pads and the present invention is thus not limited to sanitary napkins. The most significant difference between these various types of absorbent articles and sanitary napkin 11 is the overall shape and size of the article. These absorbent articles should be configured so as to be easily positioned in the desired location adjacent the wearer's body, and suitable shapes are well-known in the art. In the case of diapers and incontinence pads, these articles are generally designed to be secured about a waist of the wearer such that the absorbent core is positioned within the crotch adjacent to expected regions of fluid discharge. Thus, these absorbent articles may have optional leg elastic members, waist elastic members, and fasteners known to those skilled in the art. Pantyliners, on the other hand, are designed to be secured to the undergarment of the wearer with the absorbent core once again positioned adjacent the area of fluid discharge in a fashion similar to sanitary napkin 11.

The core of the absorbent articles of the present invention must acquire discharged fluids, distribute the acquired fluids to unused or unsaturated parts of the core, and store and retain the fluids even under pressure in order to both prevent the soiling of clothing adjacent to the area of discharge and to pull discharged fluid away from the wearer's skin. Of course the articles also must be comfortable to wear. Thus, the various components of the absorbent articles of the present invention are chosen with these goals in mind.

The outer surface of topsheet 13 is generally positioned in close proximity to, or in contact with the wearer's body when absorbent article 11 is employed.

Discharged bodily fluids will first contact body-facing side 14 of topsheet 13, and thus topsheet 13 should be a fluid pervious material which permits fluids to rapidly penetrate through its thickness towards absorbent core 21. Relatively hydrophobic materials having good strike-through characteristics should be employed for topsheet 13 in order to isolate the wearer's skin from discharged fluids. Any of a number of materials well-known to those skilled in the art may be employed, such as: natural or synthetic fibers; perforated films made from polyester, rayon, polyester/ rayon blends, polyethylene, polypropylene, polyolefin, or the like; or porous foams. Topsheet 13 can, for example, comprise a nonwoven web of fibers spunbonded, carded, wetlaid, meltblown, or hydroentangled. Topsheet 13 can also be treated by various compositions in order to render it more wettable and relatively less hydrophobic, thereby facilitating the flow of fluids through topsheet 13 upon discharge. Particularly suitable materials for topsheet 13 include macroscopically expanded formed films such as those described in U.S. Pat. No.'s. 4,342,314 and 4,637,819, which are incorporated herein by reference.

Backsheet 17 is fluid impervious, and thereby prevents collected fluids from moving through and escaping from absorbent core 21. Like topsheet 13, backsheet 17 may comprise any of a number of well-known materials, and the material employed is not critical to the present invention as long as it accomplishes its intended purpose. Thus, backsheet 17 is preferably a substantially hydrophobic nonwoven material such as a thin polymeric film, or a composite material such as a polymeric-coated material. Thermoplastic films of polyethylene, polypropylene, other polyolefins, or combinations thereof are preferred, particularly those having a thickness of less than about 0.0015 inches.

Backsheet 17 may also be embossed or matted to provide a cloth-like appearance.

Absorbent core 21 may likewise be made of any of a number of materials which are capable of absorbing and storing fluids which pass through topsheet 13. Speed of absorption, storage capacity, the ability to retain fluids under pressure, and overall comfort are all critical to the performance of absorbent core 21. Absorbent core 21 may be manufactured in a wide variety of sizes and shapes, depending upon the particular application for the absorbent article. For most absorbent articles, it is preferable that the absorbent core correspond in shape to that of topsheet 13 and backsheet 17, such as shown in FIGS. 1 and 2. In this manner, the capacity of absorbent core 21 is maximized in relation to the overall dimensions of the absorbent article.

Absorbent core 21 may be manufactured from a wide variety of hydrophilic materials commonly employed in absorbent articles, such as non-woven fibrous structures, polymeric foams, superabsorbent polymers such as absorbent gelling materials, and other equivalent materials or combinations thereof. Preferably, absorbent core 21 will quickly pull or drain fluids from topsheet 13 ("dewater"), and wick these fluids both towards backsheet 17 and radially away from the area of discharge in order to maximize the absorption capacity of core 21. In this manner, the discharged fluids are continually drained from topsheet 13 into the interior of absorbent core 21. The fluids should also be retained in absorbent core 21, even when pressure is applied to the absorbent article by normal bodily movement such as sitting. Likewise, the fluid capacity of absorbent core 21 is also preferably maximized.

Preferred materials for absorbent core 21 include non-woven webs of hydrophilic or hydrophilized natural or synthetic fibers such as cellulosic fibers (e.g., wood pulp), polyester or rayon. Airlaid wood pulp is particularly preferred, and is also known in the art as airfelt. Open-celled polymeric foams may also be employed, as well as various types of superabsorbent materials such as inorganic or organic absorbent gelling materials ("AGM"). Because of the gel blocking problem noted previously, as well as its cost, AGM is often employed as particles dispersed throughout a second absorbent material such as airfelt. Suitable superabsorbent materials are described in U.S. Pat. No. 5,360,420, which is incorporated herein by reference. Particularly preferred AGM's include NALCO 1180, a polyacrylate manufactured by the Nalco Chemical Co., of Naperville, Ill.

The optimization of the speed of absorption and wicking capability of the hydrophilic materials employed in core 21 often comes at the expense of storage capacity and retention under load, and vice versa. In order to maximize both fluid acquisition and storage, therefore, multiple layers or regions may be employed for absorbent core 21 wherein the fluid acquisition and storage properties of each layer or region differ from one another. The uppermost layers or regions of the absorbent core (i.e., those nearer to topsheet 13) are typically optimized for fluid acquisition, and should have good dewatering and wicking capabilities in order to pull fluids from topsheet 13 and transport these fluids towards the lower layers of the core. The acquisition layers or regions should also distribute the fluids radially from the discharge area in order to utilize as much core volume as possible, and may also filter and store any solid materials present in the fluids. The lowermost layers or regions of the absorbent core (i.e., those nearer to backsheet 17) are usually optimized for fluid storage capacity, and are in fluid communication with the acquisition layers or regions in order to take up fluids passing therethrough. The absorbent article of the present invention shown in FIGS. 1 and 2 utilizes this multi-layer or multi-region construction, and absorbent core 21 therefore comprises an acquisition layer 23 and a storage layer 24. Acquisition layer 23 generally comprises an absorbent material with a high fluid acquisition capability, such as airfelt. In this manner, fluids are pulled away from topsheet 13 through acquisition layer 23 towards storage layer 24. Storage layer 24 generally comprises a material having a higher fluid-retaining capability than acquisition layer 23, and may comprise, for example, an absorbent gelling material, either alone or in combination with another absorbent material. In one embodiment, storage layer 24 may comprise particles of AGM dispersed in airfelt.

Figure 3:
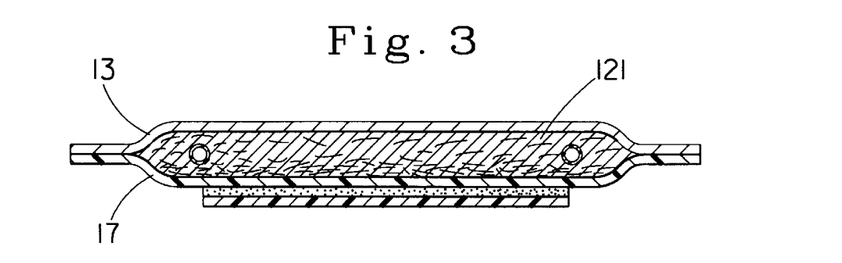
FIG. 3 is a cross-sectional view of an alternative embodiment of a sanitary napkin according to the present invention.

As an alternative to discreet layers, the embodiment of FIG. 3 has an absorbent core having an acquisition region 43 and a storage region 44 which are not precisely delineated. Acquisition region 43, for example, may comprise airfelt of lower fiber density and larger pores, as compared to storage region 44. In this manner, acquisition region 43 has a higher wicking rate than storage region 44, and in turn storage region 44 has a higher storage capacity than acquisition region 43. Alternatively, the absorbent core of FIG. 3 may comprise airfelt having AGM dispersed therein, wherein the AGM concentration is highest in storage region 44. This latter embodiment is particularly useful for diapers.

The present invention is not limited, however, to only two layers or regions for the absorbent core, and thus it is understood that any number of layers or regions of the same or varying properties may be employed. Thus, a homogeneous core may also be employed such that two "regions" of the core only differ by location (e.g., an upper region and a lower region). For example, the absorbent core can comprise a laminate of AGM and tissue, wherein the tissue helps to maintain the integrity of the AGM core. This embodiment is particularly useful for thin feminine hygiene products.

Whether multi-layer or homogeneous absorbent cores are employed, it is desirable to utilize as much of the core as possible for fluid acquisition and storage. Thus the rate of transfer of fluid from one region of the core to another must be maximized. Since fluid is typically discharged by the wearer in a single location in relation to the absorbent article, the absorbent article may have difficulty in handling this localized fluid load. For example, fluid entering the core may not be wicked away fast enough to keep up with the rate of discharge. In addition, as the absorbent core becomes more saturated, wicking and absorption rates will be reduced. Thus, it is desirable to provide a means for quickly transporting the fluids from one region of the absorbent core to another.

This is particularly true when AGM's are employed, as they are subject to the gel blocking previously described wherein the AGM particles or layer first contacted by fluids swells to such an extent that further absorption of fluids is restricted. When this occurs, the lowermost regions of the absorbent core (i.e., those regions nearest to the backsheet) are not effectively utilized and the absorbent article will fail prematurely.

The present invention overcomes these shortcomings by providing a mechanism by which fluids may be quickly transported from one region of the absorbent core to another region without relying on the wicking properties of the absorbent core material. As shown in FIG. 1, this mechanism comprises a fluid-pumping element disposed between topsheet 13 and backsheet 17. This fluid-pumping element comprises a resilient tubular member 33 which is preferably at least partially disposed within absorbent core 21.

Figure 4:
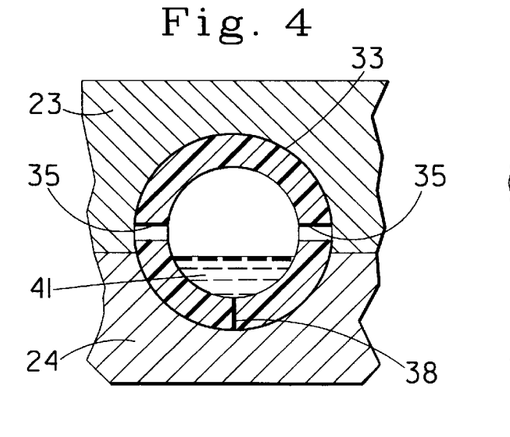
FIG. 4 is an enlarged cross-sectional view of the resilient tubular member employed in accordance with the present invention, along with a portion of the absorbent core.
Figure 5:
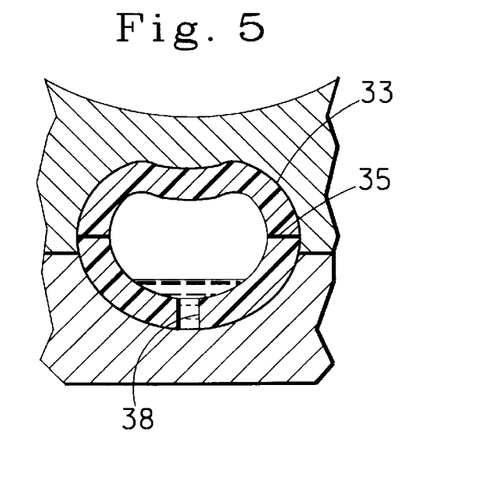
FIG. 5 is the same view as in FIG. 4, however, the tubular member has been compressed, thereby closing the fluid inlets and opening the fluid outlets.
Figure 10:
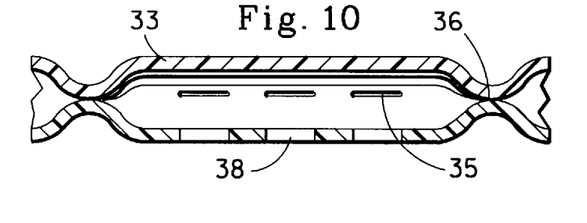
FIG. 10 is a cross-sectional view of a tubular member according to the present invention, taken along its longitudinal length.

As best shown in FIGS. 4, 5 and 10, tubular member 33 preferably has a plurality of fluid inlets 35 extending along either side of tubular member 33, and a plurality of fluid outlets 38 are provided along the bottom of tubular member 33. Tubular member 33 is preferably resilient in nature, and, as shown in FIG. 4, fluid inlets 35 are normally open when no distortive or compressive force is applied to tubular member 33. In this manner, inlets 35 provide fluid communication between the interior and exterior of the tubular member when the tubular member is uncompressed, thereby permitting fluids 41 to enter the interior of tubular member 33. In contrast, fluid outlets 38 preferably remain substantially closed when no compressive force is applied to tubular member 33. Alternatively, fluid outlets may be constructed so as to remain open even when no distortive or compressive force is applied to tubular member 33, thereby allowing the tubular member to continually drain.

When a distortive or compressive force is thereafter applied to the top portion of tubular member 33, conventional structural dynamics dictate that fluid inlets 35 will close (via downward compressive force) and fluid outlets 38 will preferably open (via outward, or spreading, tension). When this occurs, fluids 41 contained within the interior of tubular member 33 escape via fluid outlets 38 into the region of the absorbent core adjacent fluid outlets 38. These fluids may then be absorbed by core 21. Fluids not only drain through outlets 38, but are also expelled due to the compressive force. In this manner, fluids are transferred from a point adjacent inlets 35 to a point adjacent outlets 38, thereby effectuating a fluid transfer which does not rely on the wicking properties of the absorbent material of the core, and which improves core utilization.

When the compressive force is removed from tubular member 33, fluid outlets 38 preferably automatically close (or may alternatively remain open), while fluid inlets 35 open, thereby once again permitting fluids to enter the interior of tubular member 33 via inlets 35. The compression/decompression cycle also provides a suction force due to the increasing volume of the interior of tubular member 33 as the compressive force is removed. This suction pressure acts to draw additional amounts of fluid into the interior of tubular member 33 through inlets 35, thereby improving the fluid transfer capabilities of tubular member 33. Repeated compression/decompression cycles are produced by normal bodily movements of the wearer such as sitting or rocking, and thus no external means is necessary to accomplish the fluid pumping (i.e., "passive pumping").

When the length of tubular member employed extends more than a short distance (e.g., more than a few centimeters), it is preferable that tubular member be segmented as shown in FIG. 10 in order to ensure proper fluid transfer. Thus, welds 36 are provided at periodic locations along the length of tubular member 33 in order to provide segments, or discrete compartments, in tubular member 33 which are isolated from one another. These segments are preferably between about 1 and about 5 cm in length, most preferably about 3 cm, and ensure that fluids will be expelled when the requisite downward force is applied to the top of tubular member 33. If tubular member 33 is not segmented, fluids will tend to spread throughout the tubular member rather than being expelled through the fluid outlets. In addition, suction pressure upon release of the compressive force will be reduced. When tubular member 33 is a thermoplastic material, welds 36 may be readily provided merely by crimping the tubular member in the desired location with the application of heat. Alternatively, tubular member 33 may be segmented by means of external clamps, internal plugs, adhesives or other means which will be apparent to those skilled in the art.

Tubular member 33 should of course be positioned between topsheet 13 and backsheet 17 in order to be effective. In addition, fluid outlets 38 are disposed nearer to backsheet 17 than fluid inlets 35 so that normal bodily movements will provide the compression/decompression cycles necessary for fluid pumping. The fluid outlets should also be positioned at least adjacent to absorbent core 21 so that expelled fluids will be immediately absorbed by the core. Preferably, tubular member 33 is disposed at least partially within absorbent core 21, or entirely within the absorbent core as shown. The fluid inlets preferably extend along one or both sides of the tubular member, however the inlets may be positioned along the top portion (i.e., the body facing side) of the tubular member.

The most significant advantage of tubular member 33 is that it provides a pumping mechanism for quickly transporting fluids from one region of the absorbent core to another. Thus, as shown in FIGS. 4 and 5, fluid inlets 35 may be positioned within an acquisition layer 23, while fluid outlets 38 are positioned well within storage layer 24. In this manner, fluids can be quickly transferred from acquisition layer 23 to a region deep within storage layer 24 without having to first permeate through the uppermost portions of storage layer 24. This can be particularly significant when storage layer 24 comprises an absorbent gelling material which is subject to gel blocking. If fluids can be quickly distributed to a greater volume of the absorbent gelling material, gel blocking can be avoided and the storage capacity of the absorbent core more efficiently utilized.

Even when a multilayer construction is not employed for the absorbent core, as shown in FIG. 3, tubular members 33 are still advantageous for insuring a more even distribution of fluids. When absorbent cores of this type are employed, the absorbent article may fail if the fluids are not absorbed downwardly through the core as fast as they are discharged from the wearer's body due to localized overload. The provision of tubular member 33, however, acts to expedite the downward transfer of fluid in the absorbent core, thereby lessening the likelihood of premature failure. The more rapid transfer of fluids from the uppermost regions of absorbent core 121 to the lowermost regions results in a faster removal of the discharged fluids away from the wearer's body. Thus, tubular member 33 acts to transfer fluids from one region of the core to another, without relying upon the wicking properties of the core to accomplish this transfer.

Figure 9:
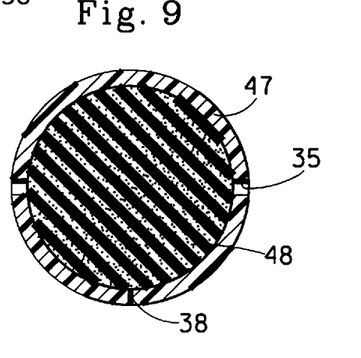
FIG. 9 is a cross-sectional view of yet another alternative embodiment of a tubular member made in accordance with the invention.

Tubular member 33 may be produced from any of a number of flexible materials, including resilient polymers such as PVC-based tubing (sold under the tradename Tygon, for example, a trademark of the Norton Co.). Alternatively, tubular member 33 may be manufactured of a thin thermoplastic film such as polyethylene or other polyolefin, with resiliency provided by an internal filler material. In the embodiment shown in FIG. 9, the tubular member comprises a thin outer layer of polyethylene 48, and an internal coarse open-celled polymeric foam 48. This polymeric foam may comprise, for example, polyurethane foam or foams formed from polymerized water-in-oil emulsions, and does not interfere with fluid pumping because of its coarse open-celled nature.

Figure 6:
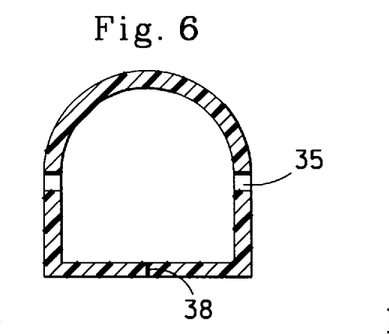
FIG. 6 is a cross-sectional view of an alternative embodiment of a resilient tubular member made in accordance with the present invention.

The tubular member may be of a number of different cross-sectional shapes, including a substantially round exterior. Alternatively, the performance of the tubular member may be tuned or enhanced by providing a non-circular cross-section such as the embodiment shown in FIG. 6 having a flattened bottom portion. Other irregular cross-sections may be employed, as long as the one-way pumping action is not interfered with, and alternative cross-sections may also ease manufacturing and conversion of existing manufacturing equipment.

One or more lengths of tubular member 33 may be provided, and one preferred configuration is shown in FIG. 1 wherein tubular member 33 extends about the periphery of the absorbent article as well as across the center section. Alternatively, one or more lengths of tubular member 33 may extend lengthwise in the "machine-direction" in the central area of the absorbent article. Numerous other alternative configurations will be apparent to those skilled in the art, and thus the present invention is not limited to the embodiment shown in FIG. 1. When the tubular member extends about the periphery of the absorbent article as in FIG. 1, the tubular member will also provide side-soiling protection since it will not only transfer fluids reaching the edge of the article to lower regions of the core from which side soiling is less likely, but it may also act as a fluid barrier and a gasket against the wearer's skin. The added rigidity of the tubular member will also help alleviate bunching of the absorbent article, which often leads to premature failure.

When tubular members extending across the interior of the absorbent article are employed such as in FIG. 1, these cross members will further act to maintain the desired form of the article.

Fluid inlets 35 and outlets 38 may be of any shape, including radial or inclined slits of a straight, curvilinear, or v-shape. The only requirements are that the inlets remain open for fluid flow-through, and the outlets preferably remain closed, when no compressive force is applied to the tubular member, and that the inlets close and the outlets open (or remain open) when a compressive force is applied to the top of the tubular member. Any shape or style of opening which accomplishes these requirements may be employed for the inlets and outlets. As shown in FIG. 10, inlets 35 preferably have a rectangular or oval shape of sufficient width to allow fluid flow to the interior of the tubular member. Inlets 35 are also oriented such that the length of slits 35 is substantially parallel to the longitudinal axis of tubular member 33. Likewise, fluid outlets 38 may comprise a slit or other suitably narrow opening, and in the preferred embodiment of FIG. 10, outlets 38 are also oriented such that the length of slits 35 is substantially parallel to the longitudinal axis of tubular member 33. The fluid outlets may alternatively comprise a series of regularly or irregularly shaped holes. The inlets and outlets may be formed during the casting, extrusion or molding of the tubular member, or by slitting, punching or hot-stamping pre-made tubing.

Figure 7:
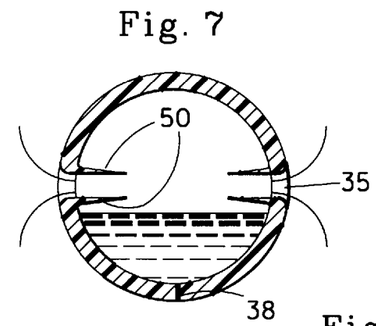
FIG. 7 is cross-sectional view of an alternative embodiment of a resilient tubular member in accordance with the present invention, wherein the tubular member is shown in an uncompressed state with bodily fluids contained therein.
Figure 8:
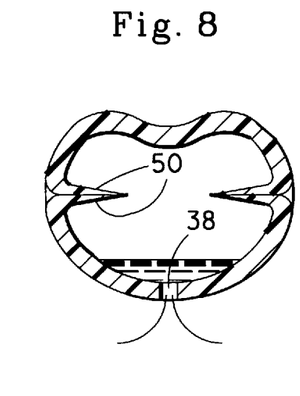
FIG. 8 depicts the tubular member of FIG. 7 in its compressed state, wherein the fluid inlets are closed and the fluid outlet is open for the discharge of fluids from the interior of the tubular member.

As shown in FIGS. 7 and 8, the fluid inlets and/or outlets may further comprise one or more check valve members associated therewith. These check valve members may comprise one or more flaps 50 which extend away from the interior or exterior surface of the tubular member adjacent a fluid inlet or outlet, and the check valve members operate in conjunction with the opening and closing of the inlets and outlets to prevent fluid flow in the undesired direction. Thus, as shown in FIG. 8, when the tubular member is compressed, the increased pressure within the tubular member will cause flaps 50 to close and thereby prevent fluids from flowing through inlets 35. Alternatively, a single flap positioned adjacent inlets 35 and sized to cover the entirety of inlets 35 may just as effectively be provided. If desired, similar flaps or other check valve elements can be provided in conjunction with outlets 38 in order to prevent fluid flow through the outlets into the interior of the tubular member. When flaps are employed adjacent the fluid outlets, the flaps preferably extend away from the exterior surface of the tubular member. Check valve flaps 50 can be formed in any of a number of ways, and may comprise resilient film material.

The absorbent articles of the present invention may be produced by conventional means, and the placement of the tubular member may be incorporated into these conventional processes. For example, absorbent airfelt cores are typically produced using molds having a shape corresponding to the desired core configuration. The tubular members of the present invention can be merely placed in the desired location within the mold prior to the application of the absorbent core material.

The foregoing description of preferred embodiments is by no means exhaustive of the variations in the present invention that are possible, and has been presented only for purposes of illustration and description. Obvious modifications and variations will be apparent to those skilled in the art in light of the teachings of the foregoing description without departing from the scope of this invention. For example, the tubular member may be placed in any of a number of various locations within the absorbent article, and variously shaped and sized openings may be employed for the fluid inlets and outlets. Thus, it is intended that the scope of the present invention be defined by the claims appended hereto.

What we claim is:

1. An absorbent article useful for absorbing discharged bodily fluids, said article comprising:
   (a) a fluid pervious topsheet;
   (b) a fluid impervious backsheet affixed to said topsheet;
   (c) an absorbent core disposed between said topsheet and said backsheet; and
   (d) a tubular member disposed between said topsheet and said backsheet for delivering said fluids to a predetermined region of said core, said tubular member having a plurality of fluid inlets and a plurality of fluid outlets, said inlets and outlets providing fluid communication between the interior and exterior of said tubular member;
wherein said tubular member is configured so as to permit said bodily fluids to pass through said inlets into the interior of said tubular member, and thereafter out of said interior through said outlets into said predetermined regions of said core.

2. The absorbent article of claim 1, wherein said tubular member is positioned at least partially within said absorbent core.

3. The absorbent article of claim 2, wherein said tubular member is positioned entirely within said absorbent core.

4. The absorbent article of claim 2, wherein said core further comprises:
   (a) a fluid storage layer; and
   (b) a fluid acquisition layer positioned between said storage layer and said topsheet;
wherein said inlets on the tubular member are positioned adjacent said acquisition layer, and said outlets on the tubular member are positioned adjacent said storage layer, such that fluid exiting the interior of the tubular member through said outlets is discharged into said storage layer.

5. The absorbent article of claim 1, wherein said tublar member is resilient, and said inlets are substantially open when no distortive force is applied to said tublar member, thereby permitting said fluids to enter the interior tublar member through said inlets.

6. The absorbent article of claim 5, wherein said outlets are normally closed, and are selectively opened in response to a distortive force applied to said tubular member thereby permitting fluids to exit from the interior of said tubular member through said fluid outlets.

7. The absorbent article of claim 6, wherein said inlets are selectively closed in response to a distortive force, such that repeated application and removal of a distortive force to said tubular member results in the transportation of said fluids through said inlets into the interior of said tubular member, and thereafter out of said interior through said outlets.

8. The absorbent article of claim 7, wherein said tubular member comprises a top, a pair of sides, and a bottom, and wherein said inlets comprise slits having a length which is substantially parallel to the longitudinal axis of said tubular member and extend along at least the top or one side of said tubular member, and said outlets comprise slits having a length which is substantially parallel to the longitudinal axis of said tubular member and extends across the bottom of said tubular member, such that a compressive force applied to the top of said tubular member will cause said inlets to substantially close and said outlets to substantially open.

9. The absorbent article of claim 7, wherein said tubular member has a plurality of compartments.

10. The absorbent article of claim 7, wherein said tubular member has a substantially round exterior cross-section.

11. The absorbent article of claim 7, wherein said article is configured to be positioned in the crotch region of a wearer such that said distortive force may be supplied by normal bodily movements.

12. The absorbent article of claim 1, wherein said tubular member is configured such that a distortive force applied to said tubular member will cause fluid contained within the interior of said tubular member to be expelled through said outlets.

13. An absorbent article useful for absorbing discharged bodily fluids, said article comprising:
   (a) a fluid pervious topsheet;
   (b) a fluid impervious backsheet affixed to said topsheet;
   (c) an absorbent core disposed between said topsheet and said backsheet; and
   (d) a resilient tubular member disposed between said topsheet and said backsheet for transporting said fluids to a predetermined region of said core, said tubular member having a plurality of fluid inlets and a plurality of fluid outlets, said inlets and outlets providing fluid communication between the interior and exterior of said tubular member;
wherein said fluids may be transported from regions adjacent said inlets into the interior of said tubular member, and thereafter through said outlets to said predetermined regions of said core adjacent said outlets.

14. The absorbent article of claim 13, wherein said inlets are substantially open and said outlets are substantially closed when no compressive force is applied against the exterior of said tubular member, and wherein said outlets are substantially open when a compressive force is applied against the exterior of said tubular member, such that each cycle of compression and decompression of said tubular member will result in said transporting of said fluids.

15. The absorbent article of claim 14, wherein said tubular member comprises a top a pair of sides and a bottom, and wherein said inlets extend along at least the top or one side of said tubular member and said outlets extend along the bottom of said tubular member, such that a compressive force applied to the top of said tubular member will cause said inlets to substantially close and said outlets to substantially open thereby expelling any fluids present in said tubular member.

16. The absorbent article of claim 15, wherein said tubular member is positioned such that normal use of said article will cause said compression and decompression of the tubular member.

17. The absorbent article of claim 14, wherein said tubular member is positioned at least partially within said absorbent core.

18. The absorbent article of claim 17, wherein said tubular member is positioned entirely within said absorbent core.

19. The absorbent article of claim 14, wherein said inlets comprise a check-valve flap configured so as to prevent fluids from escaping the interior of said tubular member through said inlets when said tubular member is compressed.

20. The absorbent article of claim 14, wherein said outlets comprise a check-valve flap configured so as to prevent fluids from passing through said outlets into the interior of said tubular member.

21. The absorbent article of claim 14, wherein said tubular member has a plurality of compartments.

22. The absorbent article of claim 14, wherein said tubular member comprises a length of resilient polymeric tubing.

23. The absorbent article of claim 14, wherein said tubular member comprises a thin polymeric film surrounding a porous internal filler material, such that said filler material comprises the interior of said tubular member and wherein said inlets and outlets are formed in said film.

24. The absorbent article of claim 14, wherein said tubular member is positioned adjacent the periphery of said absorbent article.

25. The absorbent article of claim 13, wherein said tubular member is configured such that a compressive force applied to said tubular member will cause fluid contained within the interior of said tubular member to be expelled through said outlets.

* * * * *

UNITED STATES PATENT AND TRADEMARK OFFICE
CERTIFICATE OF CORRECTION

PATENT NO. : 5,769,834
DATED      : June 23, 1998
INVENTOR(S) : Godfrey Reiter et al.

It is certified that error appears in the above-identified patent and that said Letters Patent is hereby corrected as shown below:

Claim 5, column 11, line 42, after "interior", insert --of said--.

Signed and Sealed this

Fifteenth Day of September, 1998

Attest:

BRUCE LEHMAN

Attesting Officer

Commissioner of Patents and Trademarks